(12) United States Patent
Bender et al.

(10) Patent No.: US 9,498,646 B2
(45) Date of Patent: Nov. 22, 2016

(54) COLLIMATOR FOR REDIRECTING COMPTON SCATTERED RADIATION IN STEREOTACTIC RADIOSURGERY

(71) Applicant: Wisconsin Alumni Research Foundation, Madison, WI (US)

(72) Inventors: Edward T. Bender, Madison, WI (US); Andrew J. Shepard, Waukesha, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 181 days.

(21) Appl. No.: 14/458,932

(22) Filed: Aug. 13, 2014

(65) Prior Publication Data

US 2016/0045767 A1 Feb. 18, 2016

(51) Int. Cl.
*G21K 1/02* (2006.01)
*A61N 5/10* (2006.01)
*A61B 19/00* (2006.01)
*G21K 1/06* (2006.01)
*G21K 1/10* (2006.01)

(52) U.S. Cl.
CPC .............. *A61N 5/1045* (2013.01); *A61B 19/20* (2013.01); *G21K 1/025* (2013.01); *G21K 1/067* (2013.01); *G21K 1/10* (2013.01); *A61B 2019/207* (2013.01); *A61N 2005/1095* (2013.01)

(58) Field of Classification Search
CPC ............ A61N 5/1045; A61N 2005/1095; A61B 19/20; A51B 2019/20; G21K 1/025; G21K 1/067; G21K 1/10
USPC ........................................ 378/145–147, 149
See application file for complete search history.

(56) References Cited

U.S. PATENT DOCUMENTS 5,008,911 A * 4/1991 Harding ........... G01N 23/20091
378/147
2014/0183343 A1 7/2014 Zacharopoulos et al.

* cited by examiner

*Primary Examiner* — Courtney Thomas
(74) *Attorney, Agent, or Firm* — Quarles & Brady, LLP

(57) ABSTRACT

A collimator assembly for use with radiation therapy systems, in particular stereotactic radiosurgery ("SRS") systems, is provided. In general, the collimator assembly includes a collimator in which a plurality of concentric, conical slits is formed. Each conical slit is oriented along a different slit angle, such that radiation impinging on the top surface of the collimator is redirected along each conical slit towards a common target isocenter located at a distance away from the bottom surface of the collimator. The conical slits can be referred to as "Compton slits" because they are designed to increase the radiation output at the isocenter of the collimator by redirecting Compton scattered radiation towards the isocenter in the target region. The collimator assembly thus improves the efficiency of a radiation treatment system by utilizing Compton scattered radiation that would otherwise be lost.

19 Claims, 4 Drawing Sheets

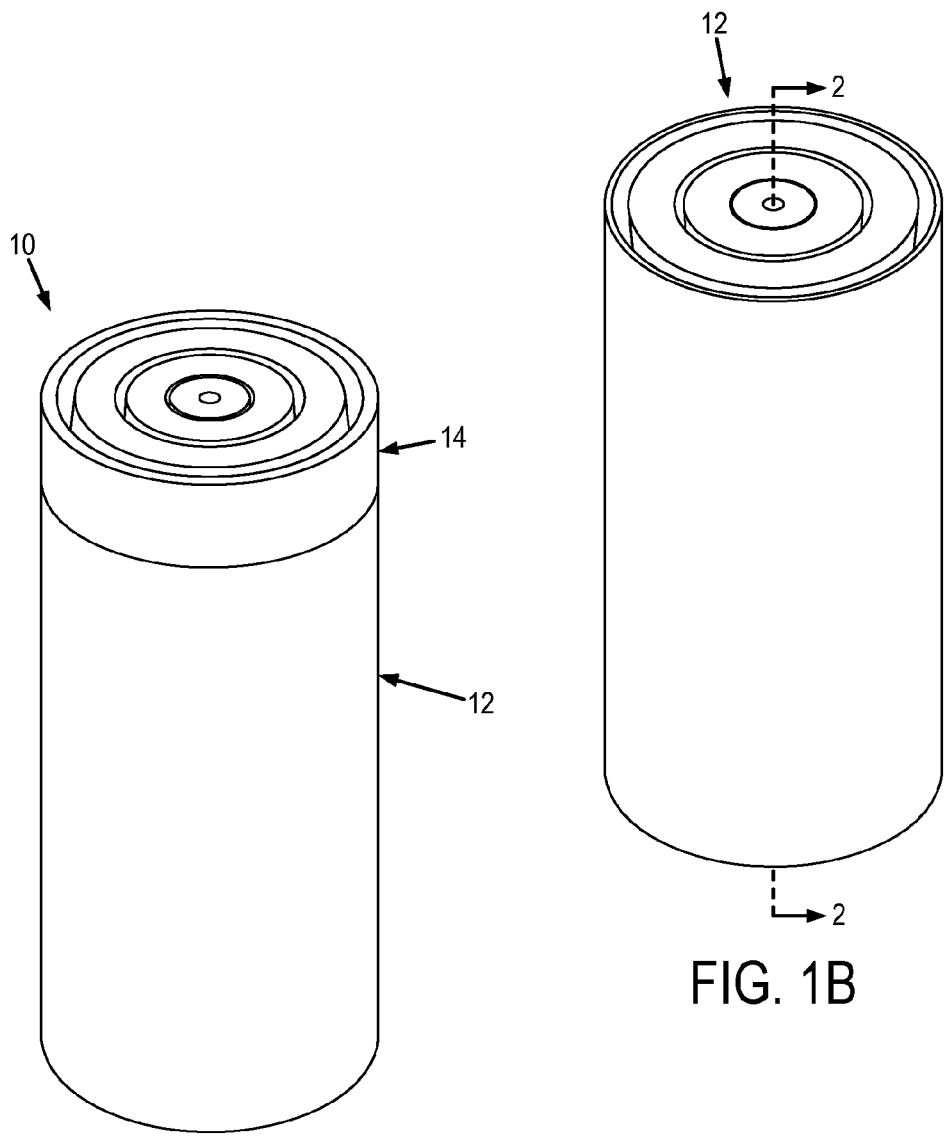
FIG. 1A
FIG. 1B
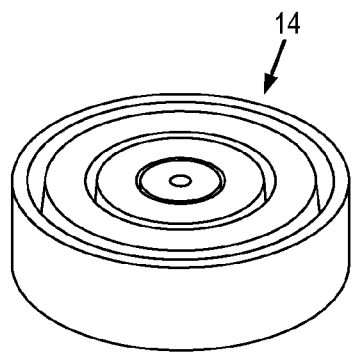
FIG. 1C

COLLIMATOR FOR REDIRECTING COMPTON SCATTERED RADIATION IN STEREOTACTIC RADIOSURGERY

BACKGROUND OF THE INVENTION

The field of the invention is external beam radiation therapy systems. More particularly, the invention relates to collimators for use in radiation treatment systems, including stereotactic radiosurgery ("SRS") systems.

SRS is a single fraction radiation therapy technique that uses x-ray radiation in order to deliver a high dose to a localized treatment region. For a standard linear accelerator radiosurgery treatment based on CT localization, it has been shown that the irradiation of a target has a positional accuracy of 0.8 mm in any direction. This offers an advantage as opposed to other radiotherapy techniques in that SRS is able to provide a large dose to a small target region while sparing much of the normal tissue surrounding the tumor. The precise localization of radiation has allowed for SRS to excel in the treatment of small tumors, particularly within the brain, such as metastases or gliomas. While the primary uses are in the brain, the application of SRS to treatments in other regions of the body, such as the liver, lungs or spinal cord, has expanded over recent years as well.

Stereotactic radiosurgery does not come without its set of drawbacks, however. A large limitation in SRS is the extent to which it can be applied to treatments. Largely, SRS can only be used for small, well defined tumors. As was mentioned previously, the treatment is highly localized in its position, and if the tumor position and extent cannot be accurately determined, the accuracy of SRS would be negated. An additional drawback associated with SRS is that the length of a single treatment may be relatively long (up to an hour for a 4 mm single isocenter treatment, and several hours for multiple isocenter treatments). This is largely due to the use of multiple isocenters for each treatment, as well as the fact that the beam is subject to a large amount of collimation in order to achieve the high accuracy associated with SRS. As the beam is being collimated down to only a few millimeters, the bulk of the radiation output from the linear accelerator is simply scatted within the collimator until it runs out of energy. Subsequently this leads to a low output reaching the patient, and thus a low efficiency.

Thus, there remains a need to enable SRS treatments in less time than is currently achievable without reducing the accuracy of the SRS treatment system or unduly limiting the therapeutic effect of the radiation dose imparted to the patient.

SUMMARY OF THE INVENTION

The present invention overcomes the aforementioned drawbacks by providing a collimator assembly that is capable of increasing the radiation delivered to a small target region by refocusing or otherwise redirecting radiation impinging on the collimator assembly that would otherwise be lost as scattered radiation.

It is an aspect of the invention to provide a collimator assembly comprising a collimator and a plurality of concentric conical slits formed in the collimator. The collimator has a top surface and a bottom surface, and each conical slit extends from the top surface of the collimator to the bottom surface of the collimator. Moreover, each conical slit has a different slit angle oriented such that radiation impinging on the top surface of the collimator is redirected along the conical slit towards a common target isocenter positioned a distance away from the bottom surface of the collimator.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 1A is an illustration of an example collimator assembly, including a collimator having Compton slits for redirecting scattered radiation towards a common target isocenter and an interaction plate that generates scattered radiation that is preferentially directed towards the Compton slits in the collimator;

FIG. 1B is an illustration of the collimator that forms a part of the collimator assembly of FIG. 1A;

FIG. 1C is an illustration of the interaction plate that forms a part of the collimator assembly of FIG. 1A;

DETAILED DESCRIPTION OF THE INVENTION

Figure 2:
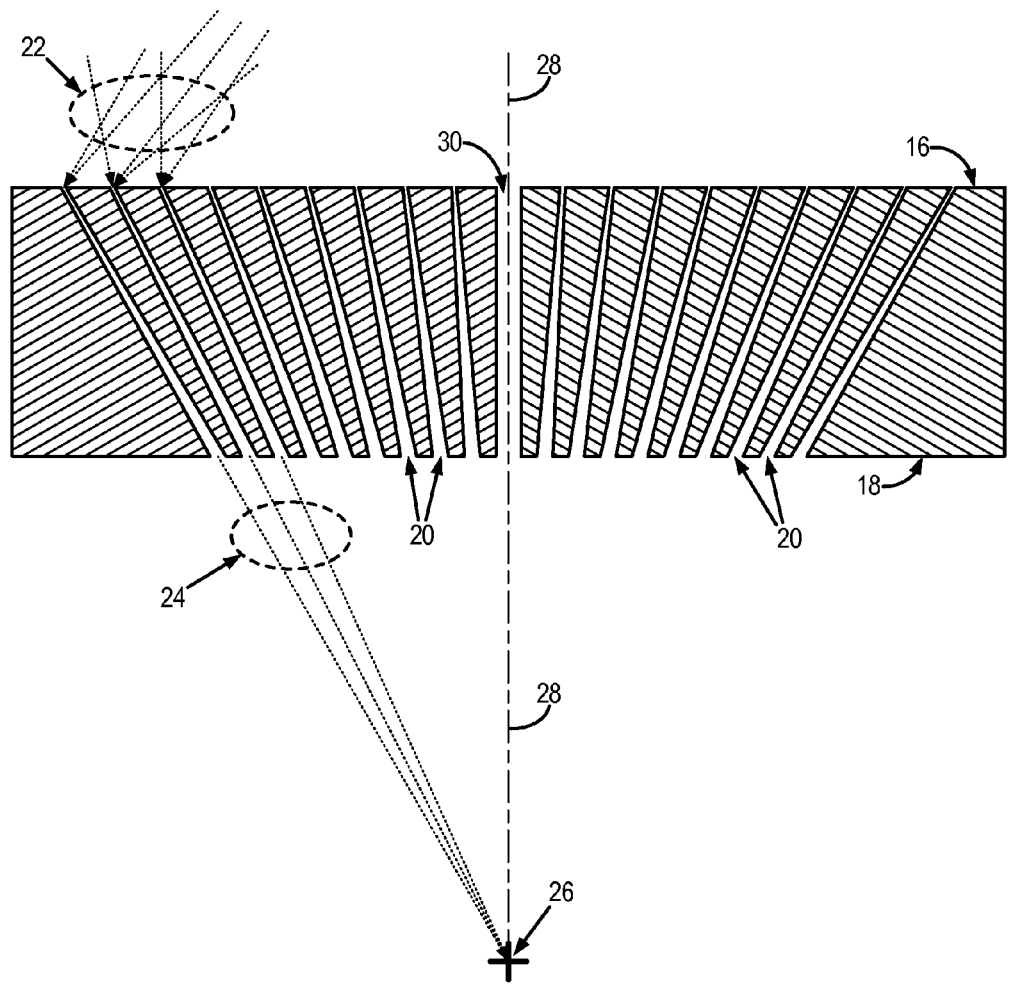
FIG. 2 is a cross section through an example collimator, in which concentric conical slits are formed for redirecting scattered radiation towards a common target isocenter.

Described here is a collimator assembly for use with radiation therapy systems, and, in particular, stereotactic radiosurgery ("SRS") systems. In general, the collimator assembly includes a collimator in which a plurality of concentric, conical slits is formed. Each conical slit is oriented along a different slit angle, such that radiation impinging on the top surface of the collimator is redirected along each conical slit towards a common isocenter located at a distance away from the bottom surface of the collimator. The conical slits can be referred to as "Compton slits" because they are designed to increase the radiation output at the isocenter of the collimator by redirecting Compton scattered radiation towards the isocenter in the target region. The collimator assembly thus improves the efficiency of a radiation treatment system by utilizing Compton scattered radiation that would otherwise be lost.

In radiation treatment systems, a larger radiation beam exits the radiation treatment system source and is then shaped into a smaller treatment beam using a collimator. Thus, the larger radiation beam is blocked in all regions except for the intended target region. As a result of this beam shaping, most of the radiation that exits the radiation source is wasted, especially for smaller treatment targets. The collimator assembly described here, however, enables some of this wasted radiation to be recaptured and redirected towards the intended target, thereby improving the operating efficiency of the treatment system.

In general, the collimator assembly is capable of significantly increasing the efficiency of previous collimator designs. It is contemplated that some configurations will be able to achieve upwards of a 50 percent gain in efficiency, which can result in reducing total treatment time by 30-35 percent. Typical treatment times vary widely based in part on the treatment target size, but, by way of example, treating trigeminal nerve can take around 45 minutes and some extreme cases of multi-isocenter radiosurgery can take 2.5 hours. The collimator assembly described here can significantly reduce these treatment times while maintaining the high spatial accuracy required of SRS treatment systems, which allows for greater normal tissue sparing.

During SRS treatments, a majority of the photons incident upon the collimator are simply scattered around the collimator until they lose all of their energy. While this effectively collimates the beam to a highly localized region, a consequence is a low efficiency, and subsequently longer treatment times.

Clinical photon beams are the result of electron acceleration into a target in order to produce bremsstrahlung photons. Therefore, the photons produced in the target are not of a single energy, but are in fact a distribution of energies. This being said, for a 6 MV linear accelerator (which is traditionally used for SRS), an average energy of approximately 2 MeV would be expected. This average energy is firmly in the Compton energy regime of approximately 0.5-10 MeV, which encompass much of the energy distribution produced from a 6 MV linear accelerator, where Compton interactions dominate.

Compton interactions are essentially the interaction of an incident photon with an electron, in which the photon gives a portion of its energy to the electron and they both scatter to opposite sides of the initial photons path. For the sake of simplification of the interaction analysis, it is generally assumed that the electron is unbound. Under this assumption the differential cross section for the Compton effect was able to be derived by Klein and Nishina as, $$\frac{d_e \sigma}{d\Omega_\phi} = \frac{r_0^2}{2} \left(\frac{hv'}{hv}\right)^2 \left(\frac{hv}{hv'} + \frac{hv'}{hv} - \sin^2 \phi\right) \quad (1)$$

where $r_0$ is the classical electron radius, $r_0 = 2.818 \times 10^{-13}$ cm; $hv$ is the incident photon energy; $hv'$ is the scattered photon energy; and $\phi$ is the scattered photon angle. The formula for the differential cross section can then be used to determine the relative probability that photons will scatter into a given angle for a given energy. At higher energies, it is much more probable for a photon to scatter in the forward direction. This being said, for energies associated with a 6 MV linear accelerator, it would be expected that the incident photons would Compton scatter in a forward directed manner.

Based off the forward directedness of the Compton scattered photons for energies associated with a 6 MV beam, it is expected that a significant amount of photons that are initially incident upon the solid portion of the collimator will scatter in the direction of the target region, which is very nearly in the forward direction. While these photons are likely to be of less energy after the Compton collision, the photon would still have enough energy remaining to ultimately travel to the target region and deposit energy.

Through proper collimator design and placement of Compton slits within the collimator, it is expected that the Compton scattered photons can contribute to the overall dose delivered to the patient. This is significant as the dose rate to the patient would increase, and thus the overall treatment time would decrease; effectively decreasing patient time in the clinic, as well as increasing patient throughput.

Referring now to FIGS. 1A-1C, an example of a collimator assembly 10 that includes a plurality of concentric conical slits for redirecting scattered radiation is illustrated. The collimator assembly 10 (FIG. 1A) includes a collimator 12 (FIG. 1B) and, optionally, an interaction plate 14 (FIG. 1C). A cross section of the collimator assembly 10 is illustrated in FIG. 2.

Referring now to FIG. 2, the collimator 12 has a top surface 16 and a bottom surface 18. Radiation from the treatment system source impinges on the top surface 16 of the collimator 12 and exits at the bottom surface 18 of the collimator 12. A plurality of concentric, conical slits 20 is formed in the collimator 12. Each conical slit 20 is oriented at a different slit angle, $\phi_i$, where i=1, . . . , N and N is the number of conical slits 20 formed in the collimator 12. The conical slits 20 are oriented such that radiation 22 impinging on the top surface 16 of the collimator 12 is redirected along the conical slit 20 and exits the collimator 12 at the bottom surface 18 as redirected radiation 24 that is directed towards a common target isocenter 26 of the collimator 12.

The collimator 12 is centered about a central axis 28. In some embodiments, the collimator 12 includes a central channel 30 extending from the top surface 16 to the bottom surface 18 along the central axis 28. When the collimator 12 is designed not to have the central channel 30, the collimator 12 is capable of generating a target region that is generally source-independent, which can be beneficial for treatment systems that may have larger source sizes.

Figure 3:
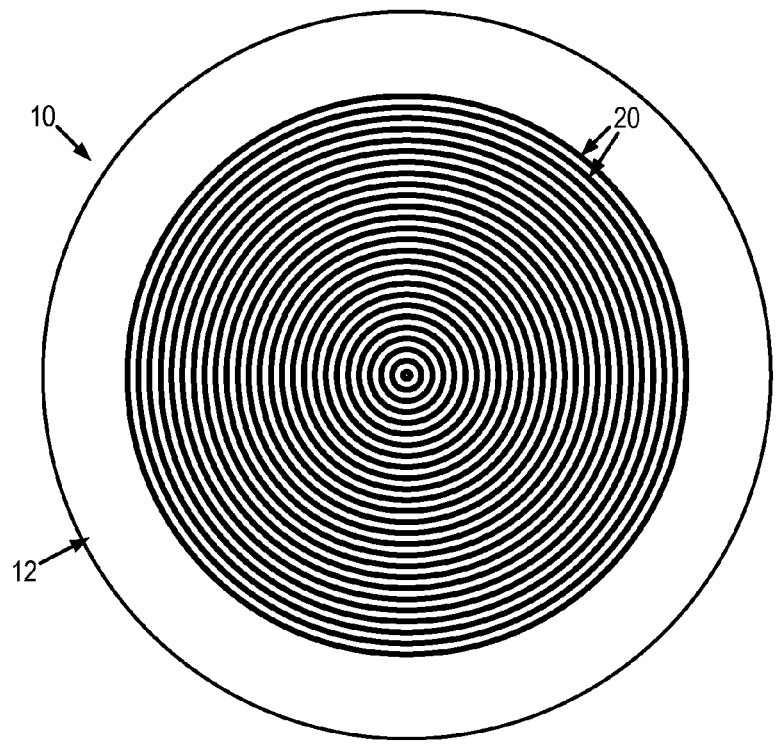
FIG. 3 is a plan view of a transverse cross section through an example collimator having concentric conical slits formed therein.

In one preferred embodiment, the collimator 12 is cylindrical with a circular cross section. An example of a cross section through a transverse plane of such a collimator 12 is illustrated in FIG. 3. In other embodiments, however, the collimator 12 can have a non-circular cross section, including an elliptical, square, or rectangular cross section. Similarly, in one preferred embodiment, the central channel 30, when present, has a circular cross section, but in some other embodiments, the central channel 30, when present, can have a non-circular cross section.

The shape of the conical slits 20 will generally define the shape of the target region. For instance, conical slits 20 that have a circular cross section will define a circular or spherical target region. Conical slits 20 that have an elliptical cross section, however, will define an elliptical or ellipsoidal target region. With this design consideration in mind, it may be possible to design a collimator assembly that achieves an anisotropic target region, which may be advantageous for treating particular anatomic regions.

The collimator 12 preferably has a uniform width along its central axis 28; however, in some embodiments the collimator may have a variable width along its central axis 28. As one example, the collimator 12 may be conically shaped, such that its width is greater at the top surface 16 than at the bottom surface 18.

Figure 4:
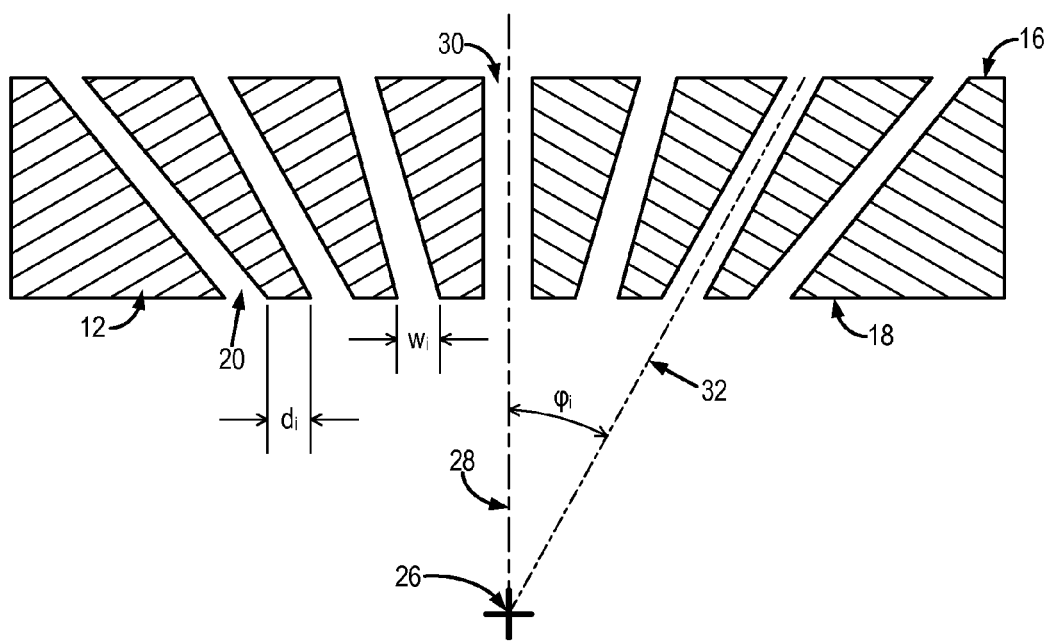
FIG. 4 is an illustration describing the slit width, slit spacing, and slit angle parameters that can be varied when designing a collimator having concentric conical slits formed therein.

An example of how the geometry of the conical slits 20 can be defined is illustrated in FIG. 4, to which reference is now made. As mentioned above, each conical slit 20 is oriented along a slit angle, $\phi_i$, such that radiation exiting the collimator 12 from a particular conical slit 20 is directed along a beam path 32 oriented along the corresponding slit angle, $\phi_i$. In general, the slit angle, $\phi_i$, can be defined as the angle from the central axis 28 of the collimator to a beam path axis 32 for a given conical slit 20, where the beam path axis 32 for a conical slit is defined as the axis extending from the center of the conical slit 20 at the top surface 16 of the collimator 12 to the center of the conical slit 20 at the bottom surface 18 of the collimator 12. As is illustrated in FIG. 3, the beam axis 32 will generally intersect the target isocenter 26 of the collimator 12.

Each conical slit has a slit width, $w_i$, and is spaced apart by a slit spacing, $d_i$. In general, the slit width, $w_i$, and the slit spacing, $d_i$, can be measured at the bottom surface 18 of the collimator 12.

In some embodiments, each conical slit 20 can be sized to have the same slit width, $w_i$=W, at the bottom surface 18 of the collimator 12. In some other embodiments, each conical slit 20 can also be sized to have a different slit width, $w_i$, at the bottom surface of the collimator 12, where i=1, . . . , N and N is the number of conical slits 20 in formed in the collimator 12.

Figure 5:
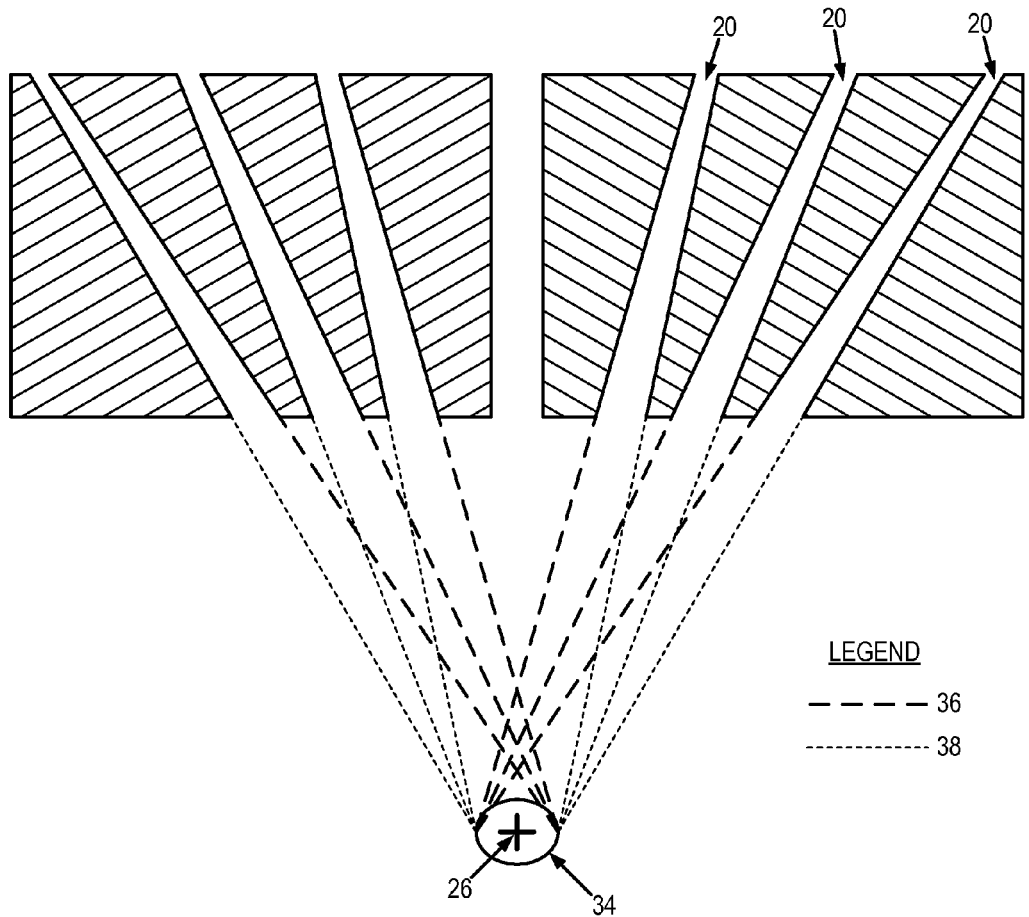
FIG. 5 is an illustration describing the relationship between conical slit width and target region size and shape.

Preferably, the slit width, $w_i$, for a given conical slit 20 is different at the bottom surface 18 of the collimator 12 than at the top surface 16. For instance, the slit width, $w_i$, can be greater at the bottom surface 18 of the collimator 12 than at the top surface 16. This geometry arises because, as illustrated in FIG. 5, the slit width, $w_i$, can be defined and designed based on the size of a target region 34 positioned at the target isocenter 26 of the collimator 12. In this example, the conical slits 20 are designed such that the inner edge of each conical slit 20 points towards the far side of the target region 34 (e.g., along dashed lines 36), while the outer edge of each conical slit 20 points towards the near side of the target region 34 (e.g., along dotted lines 38). As such, the slit width, $w_i$, at the bottom surface 18 of the collimator 12 is defined by a line 36 extending from the edge of the target region 34 to the bottom surface 18 of the collimator 12 and by a line 28 extending from the other edge of the target region 34 to the bottom surface 18 of the collimator 12. As the lines 36, 38 extend to the top surface 16 of the collimator 12, they converge and as a consequence the width of the conical slit 20 narrows.

Figure 6:
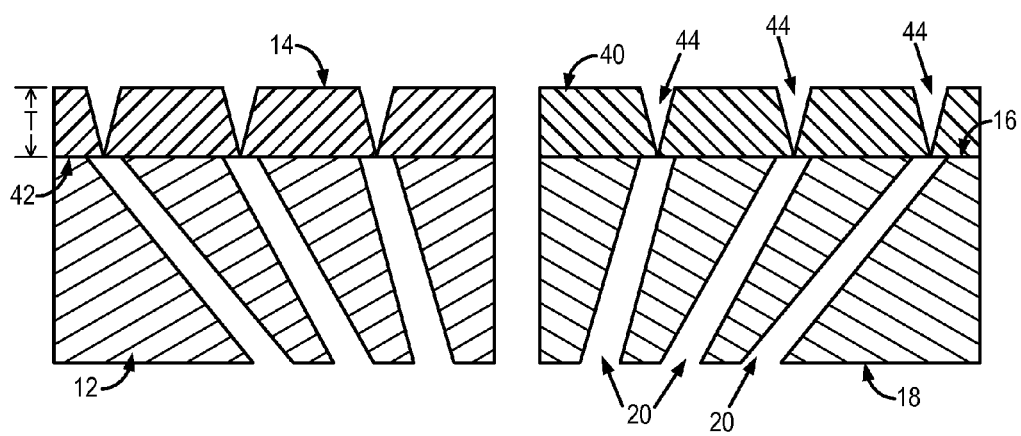
FIG. 6 is a cross section through an example collimator assembly that includes both an interaction plate and a collimator having concentric conical slits formed therein.

Referring now to FIG. 6, a cross-section of an example collimator assembly 10 that includes an interaction plate 14 is shown. The collimator assembly 10 is constructed by coupling the interaction plate 14 to collimator 12, such as by coupling the bottom surface 42 of the interaction plate to the top surface 16 of the collimator 12. In this configuration, radiation will impinge on the top surface 40 of the interaction plate 14 and exit the bottom surface 18 of the collimator 12.

In general, the interaction plate 14 is designed to provide a region in which radiation impinging on the collimator assembly 10 will interact and subsequently be scattered through the conical slits 20 in the collimator 12. The interaction plate 14 is thus useful at increasing the fluence through the collimator assembly 10. It will therefore be appreciated to those skilled in the art that although the interaction plate 14 provides the added benefit of increasing the amount of radiation transmitted through the collimator assembly 10, the collimator 12 can be used without the interaction plate 14.

Two design considerations for the interaction plate 14 are its thickness, T, and its shape. In some embodiments, the thickness, T, of the interaction plate 14 is based on the average mean free path of the entire energy distribution of the radiation impinging on the interaction plate 14. As one example, the thickness of the interaction plate 14 can be 1.65 cm. In some other embodiments, the thickness of the interaction plate 14 can be based on the average mean free path of the average energy of the radiation impinging on the interaction plate 14. As one example, the thickness of the interaction plate 14 can be 2.18 cm. In some other embodiments, the thickness of the interaction plate 14 can be based on the mean free path of the most probable energy of the radiation impinging on the interaction plate 14. As one example, the thickness of the interaction plate 14 can be 0.915 cm. It will be appreciated by those skilled in the art that the thickness of the interaction plate 14 can therefore be based in part on the material used in its construction.

In general, the interaction plate 14 can be shaped as a disk having the same cross sectional shape and dimensions as the collimator. In some embodiments, The top surface 40 and bottom surface 42 of the interaction plate 14 are generally flat; however, in some other embodiments one or both surfaces may be curved. For instance, because photons enter the collimator 12 at different angles with respect to the top surface 16 of the collimator 12, in some configurations the bottom surface 42 of the interaction plate 14 can be curved. As one example, the bottom surface 42 of the interaction plate 14 can be shaped as a very shallow parabaloid.

In some embodiments, the interaction plate 14 can be designed to increase the probability that photons will be emitted to the regions directly above the conical slits where the emitted photons can then be scattered through the conical slit and redirected towards the target region. This design consideration increases the transmission properties of the collimator assembly 10. As one example, there can be channels 44 or grooves formed in the interaction plate 14 to facilitate the generation of scattered radiation that is preferentially directed towards one of the conical slits 20. In these embodiments, the channels 44 are positioned in the interaction plate 14 such that each channel 44 is substantially aligned with a corresponding conical slit 20. In some embodiments, the channels 44 can be empty, but in other embodiments the channels may be filled with a material that facilitates the generation of scattered radiation, such as a material that facilitates the generation of Compton scattered radiation.

The collimator 12 can be composed of materials having a low melting point to allow simple construction of the device. In some embodiments, the collimator 12 can be constructed by molding the geometry of the collimator 12 using plastic and then filling the mold with powdered or melted shielding material, such as lead. In some other embodiments, the collimator 12 can be composed of a metal alloy, such as cerrobend or brass.

The collimator assembly can be manufactured using any number of different manufacturing techniques, including standard milling, electrical discharge machining ("EDM") and casting using a 3D printed negative of the collimator assembly design. When using the 3D printing method, the material or materials used for the collimator assembly preferably have a low melting point. For example, cerrobend can be used because it has a relatively low melting point of 158 degrees F., which is lower than the melting point of the 3D printing build material.

In order to properly optimize the collimator assembly design for SRS treatments with a standard linear accelerator, the setup and collimator components can be modeled and simulated using Monte Carlo N-Particle ("MCNP") transport code. As an example, variations can be made to a standard collimator design through MCNP and simulated in order to determine the optimum positioning and orientation of the conical slits to produce the most beneficial output.

In general, the size of the conical slits, as well as the slit spacing, are designed to optimize the tradeoff between the target dose and the off-axis dose. For instance, the conical slits can be designed and modified using MCNP by defining a series of individual cones and then designating the space in between the cones as the slits within the collimator. In order to make adjustments to the positioning and slope of the slits, the vertices and slope of each cone can be adjusted such that the cone lined up with the target isocenter.

In some embodiments, the slit width can be selected in the range of 0.25-0.55 cm. Preferably, the slit width should not be smaller than 0.25 cm because when the slit width decreases below 0.25 cm it may not be possible to achieve the desired dimensions for the collimator assembly to achieve appreciable results. For instance, at small slit widths, the inner and outer edges of the conical slit would overlap before spanning the desired vertical distance to allow optimal redirection of radiation impinging on the collimator assembly.

Based on a sensitivity study that measured an estimate of the conical slit width that gave the largest ratio of percentage increase in dose to the target region versus the percentage increase in dose to the off-axis region, an optimal slit width may be 0.25 cm for a 6 mm target region positioned at a source-to-axis distance ("SAD") of 100 cm.

In some embodiments, the slit spacing can be selected in the range of 0.15-0.45 cm, where the slit spacing is defined as the amount of solid material between neighboring conical slits at the bottom surface of the collimator. As a result of the conical nature and varying slope (e.g., slit angle) of each of the conical slits, the amount of material between the conical slits will generally vary along the height of the collimator.

Based on a sensitivity study that measured an estimate of the conical slit spacing that gave the largest ratio of percentage increase in dose to the target region versus the percentage increase in dose to the off-axis region, an optimal slit spacing may be 0.25 cm for a 6 mm target region positioned at a SAD of 100 cm.

Optimization of the interaction plate can be performed using a two-dimensional model of the collimator that accounts for single scattering events within the interaction plate, as well as transmission through the entire collimator. In this example, the optimization is first setup such that the geometry is split into finite voxels at both the interaction plate and the target plane. Along the target plane, one-dimensional voxels are used to create a profile and determine whether particles hitting the target plane are within or outside the target region. Conversely, the interaction plate is modeled as a series of two-dimensional voxels in which each voxel has a distinct attenuation coefficient. The attenuation coefficient of each of the voxels is used in order to determine the probability of an event occurring in a given voxel, as well as the amount of attenuation that would occur if photons were to pass through the voxel. This being said, the attenuation coefficient of each voxel affects the amount of overall attenuation and the amount of scattering.

The attenuation coefficient for each voxel in the interaction plate is modified through the use of a minimization function in order to optimize the percentage increase in the energy fluence outside of the target region relative to the percentage increase in the energy fluence within the target region. As one example, the minimization can use a sequential quadratic programming algorithm and can modify the attenuation coefficient of each voxel on a continuous basis where the solution for each voxel is constrained between zero and the attenuation coefficient of the material from which the interaction plate is to be composed. For instance, the interaction plate can be composed of a metal or metal alloy. One example of a metal alloy that can be used to construct the interaction plate is cerrobend.

Figure 7:
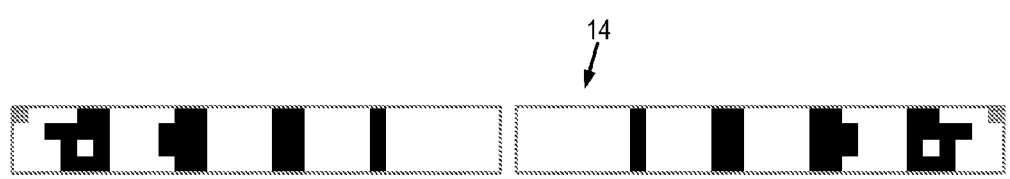
FIG. 7 is an illustration of an example interaction plate design.

An example of an interaction plate optimized using this technique, and considering only scattering, is illustrated in FIG. 7. This particular example was based on a collimator with four conical slits. The interaction plate shown in FIG. 7 has not been optimized for transmission properties, but is only provided to further understanding of the optimization process.

In FIG. 7, the white voxels correspond to regions of solid material (e.g., cerrobend), whereas the black voxels correspond to air. Based on how the minimization is set up, the optimized solution may arrive at a result with an attenuation coefficient between air and cerrobend. In that case, the resulting voxel would be colored gray. For this specific example it was generally seen that air was placed just before the regions where scattering through the slits could occur.

Based on a sensitivity study that measured an estimate of the interaction plate thickness that gave the largest ratio of percentage increase in dose to the target region versus the percentage increase in dose to the off-axis region, an optimal interaction plate thickness for an interaction plate composed of cerrobend may be 3.65 cm for a 6 mm target region positioned at a SAD of 100 cm.

Using the collimator assemblies described here, the dose rate to a target can be increased without compromising the large degree of off-axis tissue sparing inherent to SRS treatments. In general, a different collimator assembly can be designed for different treatment strategies. For instance, a given collimator assembly can be optimized for a particular treatment region size, a particular anatomy, a particular treatment system, and so on.

There are several different types of SRS treatment systems, and these systems can implement the collimator assembly described here. Some of the most highly used SRS units include the Gamma Knife system produced by Elekta and the CyberKnife system produced by Accuray.

The Gamma Knife system uses approximately 200 Cobalt-60 (average gamma energy=1.25 MeV) sources located at different external positions around the brain in order to deliver a treatment to the patient. The Gamma Knife system is exclusively used for the treatment of brain tumors or disorders, and is largely considered the "gold standard" of SRS delivery units.

In contrast to the Cobalt-60 sources of the Gamma Knife, the CyberKnife system uses a single linear accelerator for treatment. A robotic arm is used in order to position the linear accelerator and provides the CyberKnife system with the ability to treat from a wide variety of positions and angles. Additionally, the CyberKnife system incorporates image guidance which can prove to be helpful in combating target movement.

It is also common for clinics to use a standard (non-dedicated) 6 MV linear accelerator to perform SRS treatments. This method is relatively similar to that of the CyberKnife in the fact that it uses a linear accelerator; however, the linear accelerator is fixed to a gantry that rotates around the patient couch. In the use of a standard linear accelerator for SRS treatments, tertiary treatment cones must be used to collimate the beam to the desired extent. The tertiary cones are added to the system in order to create a sharp dose gradient in a small circular field. The tertiary cones used for treatments come in set sizes and generally range from 5-40 mm. The wide range of sizes allows for SRS treatments of varying applications and tumor sizes.

The present invention has been described in terms of one or more preferred embodiments, and it should be appreciated that many equivalents, alternatives, variations, and modifications, aside from those expressly stated, are possible and within the scope of the invention.

The invention claimed is:

1. A collimator assembly comprising:
 a collimator having a top surface and a bottom surface;
 a plurality of concentric conical slits formed in the collimator, each conical slit extending from the top surface of the collimator to the bottom surface of the collimator and having a different slit angle oriented such that radiation impinging on the top surface of the collimator is redirected along the conical slit towards a common target isocenter positioned a distance away from the bottom surface of the collimator.

2. The collimator assembly as recited in claim 1, wherein the plurality of concentric conical slits are each spaced apart at the bottom surface of the collimator by a same slit spacing.

3. The collimator assembly as recited in claim 1, wherein some of the plurality of concentric conical slits are spaced apart at the bottom surface of the collimator by different slit spacings than others of the plurality of concentric conical slits.

4. The collimator assembly as recited in claim 1, wherein each of the plurality of concentric conical slits has a same slit width measured at the bottom surface of the collimator.

5. The collimator assembly as recited in claim 4, wherein the slit width for a conical slit is different at the top surface of the collimator than at the bottom surface of the collimator.

6. The collimator assembly as recited in claim 1, wherein some of the plurality of concentric conical slits have different slit widths measured at the bottom surface of the collimator than others of the plurality of concentric conical slits.

7. The collimator assembly as recited in claim 1, further comprising a central bore extending along a central axis of the collimator from the top surface to the bottom surface of the collimator.

8. The collimator assembly as recited in claim 1, further comprising an interaction plate coupled to the top surface of the collimator, the interaction plate being composed of a material that scatters radiation impinging on the interaction plate towards the top surface of the collimator.

9. The collimator assembly as recited in claim 8, wherein the interaction plate includes regions that are positioned and configured to preferentially scatter radiation towards the plurality of concentric conical slits.

10. The collimator assembly as recited in claim 9, wherein the regions in the interaction plate are composed of a different material from the rest of the interaction plate.

11. The collimator assembly as recited in claim 9, wherein the regions in the interaction plate comprise channels formed in the interaction plate, the channels being shaped such that radiation impinging on the channels is preferentially scattered towards the plurality of concentric conical slits.

12. The collimator assembly as recited in claim 8, wherein the interaction plate is composed of at least one of a metal or a metal alloy.

13. The collimator assembly as recited in claim 12, wherein the interaction plate is composed of cerrobend.

14. The collimator assembly as recited in claim 1, wherein the collimator is composed of at least one of a metal or a metal alloy.

15. The collimator assembly as recited in claim 14, wherein the collimator is composed of cerrobend.

16. The collimator assembly as recited in claim 1, wherein the collimator is cylindrical.

17. The collimator assembly as recited in claim 16, wherein the collimator has a circular cross section.

18. The collimator assembly as recited in claim 17, wherein the plurality of concentric conical slits have circular cross sections.

19. The collimator assembly as recited in claim 1, wherein the collimator and the plurality of concentric conical slits are configured to redirect radiation impinging on the top surface of the collimator towards the common target isocenter for radiation energies in a range of 0.5 MeV to 10 MeV.

* * * * *